US006337196B1

(12) United States Patent
Kirchner et al.

(10) Patent No.: US 6,337,196 B1
(45) Date of Patent: Jan. 8, 2002

(54) ENZYMATIC PROCESSES FOR PREPARING (S)-CYANOHYDRINS

(75) Inventors: Gerald Kirchner, Wesel (DE); Irma Wirth, Enns (AT); Christian Werenka, Ansfelden (AT); Herfried Griengl, Graz (AT); Michael Schmidt, St. Oswald (AT)

(73) Assignee: DSM Fine Chemicals Austria Nfg GmbH & CoKG, Linz (AT)

( * ) Notice: Subject to any disclaimer, the term of this patent is extended or adjusted under 35 U.S.C. 154(b) by 0 days.

(21) Appl. No.: 09/331,761

(22) PCT Filed: May 26, 1997

(86) PCT No.: PCT/EP97/02692

§ 371 Date: Jun. 25, 1999

§ 102(e) Date: Jun. 25, 1999

(87) PCT Pub. No.: WO98/30711

PCT Pub. Date: Jul. 16, 1998

(30) Foreign Application Priority Data

Jan. 13, 1997 (AT) .............................................. A-41/97

(51) Int. Cl.[7] ................................................ C12P 13/00
(52) U.S. Cl. ...................................... 435/128; 435/280
(58) Field of Search .................................. 435/128, 280

(56) References Cited

U.S. PATENT DOCUMENTS 5,346,816 A  *  9/1994  Griengl et al. ............... 435/128
5,714,356 A  *  2/1998  Griengl et al. ............... 435/128
5,885,809 A     3/1999  Effenberger et al. ......... 435/128

FOREIGN PATENT DOCUMENTS

EP         0 539 767     *  5/1993

OTHER PUBLICATIONS

Hasslacher et al. Molecular Cloning of the Full–Length cDNA of (S)–Hydroxynitrile Lyase from *Hevea brasiliensis*, J. Biol. Chem. 271(10): 5884–5891, Mar. 8, 1996.*

F. Effenberger et al., *Tetrahedron Letters*, 31(9), 1249–1252 (1990).*

M. Hasslacher et al., *J. Biol. Chem.*, 271(10), 5884–5891 (1996).*

M. Schmidt et al., *Tetrahedron*, 52(23), 7833–7840 (1996).

* cited by examiner

*Primary Examiner*—Rebecca E. Prouty
*Assistant Examiner*—Richard Hutson
(74) *Attorney, Agent, or Firm*—Wenderoth, Lind & Ponack, LLP

(57) ABSTRACT

An enantioselective process for the preparation of the (S)-enantiomer of an optically active cyanohydrin by reaction of an aldehyde or of a ketone with a cyanide group donor, in which the aldehyde or the ketone is reacted with a cyanide group donor in an organic diluent in the presence of a recombinant (S)-hydroxynitrile lyase from *Hevea brasiliensis* and the (S)-cyanohydrin formed is isolated from the reaction mixture.

9 Claims, No Drawings

ENZYMATIC PROCESSES FOR PREPARING (S)-CYANOHYDRINS

This application is a 371 of PCT/EP97/02692 filed May 28, 1997.

Cyanohydrins are of importance, for example, for the synthesis of alpha-hydroxy acids, alpha-hydroxy ketones and beta-aminoalcohols which are used for obtaining biologically active substances, e.g. pharmaceutical active compounds, vitamins or alternatively pyrethroid compounds.

A cyanohydrin can be prepared by addition of a cyanide group to the carbonyl carbon of an aldehyde or of an unsymmetrical ketone, mixtures of enantiomers of optically active cyanohydrins resulting.

Since in a biologically active mixture of enantiomers only one of the two enantiomers is biologically active, there has been no lack of attempts to find a process for the preparation of the (S)-enantiomer of an optically active cyanohydrin in as high an optical purity as possible.

Thus, in Makromol. Chem. 186, (1985), 1755–62, for example, a process for obtaining (S)-cyanohydrins by reaction of aldehydes with hydrocyanic acid in the presence of benzyloxycarbonyl-(R)-phenylalanine-(R)-histidine methyl ester as a catalyst is described. The optical purity of the (S)-cyanohydrins obtained, however, is highly unsatisfactory.

An enzymatic process for the preparation of optically active (R)- or (S)-cyanohydrins by reaction of aliphatic, aromatic or heteroaromatic aldehydes or ketones with hydrocyanic acid in the presence of (R)-oxynitrilase (EC 4.1.2.10) from Prunus amygdalis or oxynitrilase (EC 4.1.2.11) from Sorghum bicolor is described in EP-A-0 326 063. Examples of the stereo-specific preparation of aliphatic (S)-cyanohydrins are not indicated. This is not surprising, since in Angew. Chemie 102 (1990), No. 4, pp. 423–425 it is stated by inventors who are mentioned in EP-A-0 326 063 that no aliphatic (S)-cyanohydrins can be prepared with hydrocyanic acid from the (S)-oxynitrilase from Sorghum EP 0 632 130 additionally describes a process in which aliphatic aldehydes or unsymmetrical aliphatic ketones are reacted stereospecifically with hydrocyanic acid and oxynitrilase from Hevea brasiliensis to give (S)-cyanohydrins. The reaction is carried out according to EP 0 632 130, preferably in an aqueous diluent without addition of organic solvents, since these rapidly inhibit the activity of the enzyme, as described in EP 0 632 130.

EP 0 539 767 describes a similar process for the preparation of (S)-cyanohydrins, using specific cyanide group donors instead of hydrocyanic acid. EP 0 539 767 also indicates that organic solvents rapidly inhibit the activity of the enzyme.

The use of recombinant hydroxynitrile lyase from Hevea brasiliensis in an aqueous buffer system is described in Tetrahedron Letters Vol. 52, No. 23, 1996, pp. 7833–7840.

It has now unexpectedly been found that the use of recombinant hydroxynitrile lyase (Hnl) from *Hevea brasiliensis* makes possible the reaction of a large number of carbonyl compounds, such as, for example, aliphatic, alicyclic, unsaturated, aromatically substituted aliphatic, aromatic, and also heteroaromatic aldehydes and ketones to give the corresponding cyanohydrins, the recombinant Hnl being distinguished by a high resistance to organic solvents.

The invention therefore relates to a process for the preparation of the (S)-enantiomer of an optically active cyanohydrin by reaction of an aldehyde or of a ketone with a cyanide group donor, which comprises reacting the aldehyde or the ketone with a cyanide group donor in an organic diluent in the presence of a recombinant (S)-hydroxynitrile lyase from *Hevea brasiliensis* and isolating the (S)-cyanohydrin formed from the reaction mixture.

Starting materials employed in the process according to the invention are an aldehyde or a ketone, a cyanide group donor, a recombinant hydroxynitrile lyase and a diluent.

Aldehydes are in this case understood as meaning aliphatic, aromatic or heteroaromatic aldehydes. Aliphatic aldehydes are in this case understood as meaning saturated or unsaturated aliphatic, straight-chain, branched or cyclic aldehydes. Preferred aliphatic aldehydes are straight-chain aldehydes in particular having 2 to 18 C atoms, preferably from 2 to 12, which are saturated or mono- or polyunsaturated. The aldehyde can in this case have both C—C double bonds and C—C triple bonds. The aldehyde can be unsubstituted or substituted by groups which are inert under the reaction conditions, for example by optionally substituted aryl or heteroaryl groups such as phenyl or indolyl groups, or by halogen, ether, alcohol, acyl, carboxylic acid, carboxylic acid ester, nitro or azido groups. Examples of aromatic or heteroaromatic aldehydes are benzaldehyde or variously substituted benzaldehydes such as, for example, 3-phenoxybenzaldehyde, additionally furfural, anthracene-9-carbaldehyde, furan-3-carbaldehyde, indole-3-carbaldehyde, naphthalene-1-carbaldehyde, phthalaldehydes, pyrazole-3-carbaldehyde, pyrrole-2-carbaldehyde, thiophene-2-carbaldehyde, isophthalaldehyde or pyridine aldehydes etc. Ketones are aliphatic, aromatic or heteroaromatic ketones in which the carbonyl carbon atom is identically or unidentically substituted. Aliphatic ketones are understood as meaning saturated or unsaturated, straight-chain, branched or cyclic ketones. The ketones can be saturated or mono- or polyunsaturated. They can be unsubstituted, or substituted by groups which are inert under reaction conditions, for example by optionally substituted aryl or heteroaryl groups such as phenyl or indolyl groups, or by halogen, ether, alcohol, acyl, carboxylic acid, carboxylic acid ester, nitro or azido groups. Examples of aromatic or heteroaromatic ketones are acetophenone, benzophenone etc. Aldehydes and unsymmetrical ketones are preferably reacted.

Aldehydes and ketones which are suitable for the process according to the invention are known or can be prepared in the customary manner.

A possible cyanide group donor is hydrocyanic acid or a cyanohydrin of the general formula $R_1R_2C(OH)(CN)$. In the formula I, $R_1$ and $R_2$ independently of one another are hydrogen or a hydrocarbon group which is unsubstituted or substituted by groups which are inert under the reaction conditions, or $R_1$ and $R_2$ together are an alkylene group having 4 or 5 C atoms, where $R_1$ and $R_2$ are not simultaneously hydrogen. The hydrocarbon groups are aliphatic or aromatic, preferably aliphatic groups. $R_1$ and $R_2$ are preferably alkyl groups having 1 to 6 C atoms, the cyanide group donor is very preferably acetone cyanohydrin.

The cyanide group donor can be prepared according to known processes. Cyanohydrins, in particular acetone cyanohydrin, are also commercially available.

Preferably, hydrocyanic acid or acetone cyanohydrin is employed as the cyanide group donor. The hydroxynitrile lyase employed is recombinant (S)-Hnl from *Hevea brasiliensis*. Suitable recombinant (S)-Hnl is obtained, for example, from genetically modified microorganisms such as, for example, *Pichia pastoris* or *Saccharomyces cerevisiae*. Recombinant (S)-Hnl from *Pichia pastoris* is preferably employed. By functional overexpression in the methylotrophic yeast *Pichia pastoris,* this Hnl can be obtained in any desired amount (M. Hasslacher et al., J. Biol. Chem. 1996, 271, 5884). This expression system is particularly suitable for fermentations having a high cell density. Thus, it is possible to obtain approximately 20 g of pure enzyme per liter of fermentation medium. The achievable specific activities of the purified recombinant protein are approximately twice as high as those of the natural enzyme, which was isolated from the leaves of the tree *Hevea brasiliensis.* After cell disruption, the cytosolic fraction can be used without further purification, by means of which the expenditure of work is minimized. The enzyme is not glycosylated and also has no prosthetic group which would lead to inactivation during removal of the protein moiety. The Hnl can be employed at room temperature for a number of days without significant loss of activity, and is adequately stable at −20° C. in the long term. As a result, the possibility results of using the same enzyme batch a number of times. The enzyme is also distinguished by a high resistance to solvents. The possibility therefore exists of employing organic solvents for the enzymatic reaction, which has a favorable effect on the productivity of the respective process.

The hydroxynitrile lyase can be employed in purified or unpurified form, as such or immobilized. The preparation and purification of the hydroxynitrile lyase can be carried out, for example, by precipitation with ammonium sulfate and subsequent gel filtration, for example according to D. Selmar et al., Physiologia Plantarum 75 (1989), 97–101.

The reaction according to the invention is carried out in an organic diluent. Organic diluents which can be used are water-immiscible aliphatic or aromatic hydrocarbons which are optionally halogenated, alcohols, ethers or esters.

Preferably, ethyl acetate, diisopropyl ether, methyl tert-butyl ether and dibutyl ether are used.

The (S)-Hnl can in this case be present either in immobilized form in the organic diluent, but the reaction can also be carried out in a two-phase system, using nonimmobilized (S)-Hnl, the organic diluent employed being a water-immiscible diluent such as, for example, aliphatic or aromatic hydrocarbons which are optionally halogenated, ethers or esters.

Approximately 50 to 300 g of diluent and 200 to 20,000 IU of hydroxynitrile lyase activity, preferably approximately 500 to 5000 IU, are added per g of aldehyde or ketone. An IU (International Unit) in this case expresses the formation of one micromole of product per minute and per gram of enzyme crude isolation. The amount of the respective hydroxynitrile lyase needed is best determined in an activity test, for example according to Selmar et al., Analytical Biochemistry 166 (1987), 208–211.

At least one mole, preferably 1 to 2 mol, of cyanide group donor are added per mole of aldehyde or keto group employed.

The reaction mixture is shaken or stirred at temperatures from approximately 0° C. up to the deactivation temperature of the hydroxynitrile lyase, preferably from 20 to 30° C. In the course of this, the cyanide group is transferred from the cyanide group donor to the carbonyl carbon atom of the aldehyde or ketone employed and the (S)-enantiomer of the optically active cyanohydrin corresponding to the aldehyde or ketone employed is mainly formed. The progress of the reaction can in this case be monitored, inter alia, by gas chromatography.

After reaction has taken place, the cyanohydrin formed can be extracted from the reaction mixture with the aid of an organic solvent which is not miscible with water, for example aliphatic or aromatic optionally halogenated hydrocarbons, e.g. pentane, hexane, benzene, toluene, methylene chloride, chloroform, chlorobenzenes, ethers such as, for example, diethyl ether, diisopropyl ether or esters, for example ethyl acetate or mixtures of such solvents. Should the purity of the extracted product not be adequate, a purification operation can follow. The purification can be carried out by a known method and takes place best chromatographically.

EXAMPLE 1

178 mg of 3-phenylpropanal (1.33 mmol) were dissolved in 2.8 ml of diisopropyl ether and the solution was adjusted to a temperature of 0–5° C. using a cooling bath. After addition of 1.1 ml of aqueous enzyme solution (900 IU/ml) ((S)-Hnl from *Pichia pastoris* in 50 mM phosphate buffer), the mixture was stirred at 0–5° C. for 5 min and 200 µl of anhydrous hydrocyanic acid were then added rapidly in one portion. The reaction vessel was sealed pressure-tight and the solution was stirred at 0–5° C. for 2 hours. Extraction three times with 10 ml of diisopropyl ether each time, drying over anhydrous sodium sulfate, removing the solvent by distillation in vacuo and purification by column chromatography afforded the optically active cyanohydrin as a homogeneous substance (204 mg of colorless oil, 95% isolated yield), $[\alpha]_D^{20}$+7.1° (c 1.3, $CHCl_3$).

For derivatization, the purified cyanohydrin was taken up in 10 ml of dry methylene chloride and treated with 2 mol equivalents of acetic anhydride and 2 mol equivalents of pyridine. After a reaction time of 10 hours at room temperature, it was washed with 10 ml each of 5% $H_2SO_4$, distilled water and saturated sodium hydrogencarbonate solution, the organic phase was dried over anhydrous sodium sulfate and the solvent was removed in vacuo. Purification by column chromatography afforded 221 mg of (S)-(−)-2-acetoxy-4-phenylbutanenitrile as a colorless oil (86% isolated yield), $[\alpha]_D^{20}$−43.4° (c 1.95, $CHCl_3$). e.e.= 94% (determined by gas chromatography)

$^1$H-NMR: δ (ppm) 2.13 (s, 3H); 2.25 (q, 2H); 2.85 (t, 2H); 5.28 (t, 1H); 7.21–7.37 (m, 5H).

$^{13}$C-NMR: 169.13; 139.31; 128.90; 128.48; 126.80; 116.89; 60.72; 33.89; 30.88; 20.34.

EXAMPLE 2

0.4 g of microcrystalline cellulose was allowed to swell at room temperature for 1 hour in 2.7 ml of 0.02 M sodium acetate buffer and the aqueous buffer was then removed by filtration. 1.35 ml of an aqueous hydroxynitrile lyase (from *Pichia pastoris* in 50 mM phosphate buffer) solution (390 IU/ml) were added to the support pretreated in this way and the mixture was shaken at room temperature for 10 min. This suspension was then adjusted to a water content of 40% in a rotary evaporator. The enzyme immobilizate thus obtained was treated with 2.8 ml of ethyl acetate (saturated with 0.01 M sodium acetate buffer, pH 5.4) and with 141 mg of freshly distilled benzaldehyde (1.33 mmol). After addition of 5.25 mmol of anhydrous hydrocyanic acid (200 µl) the reaction vessel was sealed pressure-tight and the reaction mixture was stirred at room temperature for 1 hour. The enzyme immobilizate was then removed by means of filtration, washed three times with 5 ml of ethyl acetate each time (saturated with 0.01 M sodium acetate buffer, pH 5.4) and dried over anhydrous sodium sulfate. The solvent was removed under reduced pressure and the crude cyanohydrin obtained in this way was purified by column chromatography. 170 mg of a colorless oil (96% isolated yield) were obtained, $[\alpha]_D^{20}$−46.5° (c 1.4, $CHCl_3$).

The pure cyanohydrin was dissolved in 10 ml of dry methylene chloride and treated with 2 mol equivalents of acetic anhydride and 2 mol equivalents of pyridine. After reaction overnight, the mixture was extracted with 15 ml each of 5% $H_2SO_4$, distilled water and saturated sodium hydrogencarbonate solution and dried over anhydrous sodium sulfate. After removal of the solvent, the substance was purified by column chromatography. 221 mg of (S)-2-acetoxy-2-phenylacetonitrile were obtained as a colorless oil (99% isolated yield).

$[\alpha]_D^{20}$ −7.24° (c 2.3; $CHCl_3$) e.e.>99% (determined by gas chromatography).

$^1$H-NMR: δ (ppm) 2.16 (s, 3H); 6.42 (s, 1H); 7.48 (m, 5H).

$^{13}$C-NMR: 168.87; 131.80; 130.48; 129.32; 127.94; 116.12; 62.92; 20.54.

EXAMPLE 3

300 IU of hydroxynitrile lyase from *Pichia pastoris* were immobilized in a liquid-crystalline system consisting of di-n-butyl ether, water and a surfactant. 2 ml of di-n-butyl ether, 1 mmol of benzaldehyde (106 mg) and 3.94 mmol of anhydrous hydrocyanic acid (150 μl) were added to this enzyme preparation at 0–5° C. The mixture was stirred at 0–5° C. for 3 hours, and the organic phase was then poured off and washed three times with 5 ml of di-n-butyl ether each time. Drying with anhydrous sodium sulfate afforded a solution of the crude cyanohydrin, which was converted into the corresponding acetate directly using 2 mol equivalents of acetic anhydride and 2 mol equivalents of pyridine. After a reaction time of 8 hours at room temperature, the solution was washed with 15 ml each of 5% $H_2SO_4$, distilled water and saturated sodium hydrogencarbonate solution, dried using anhydrous sodium sulfate and the solvent was removed under reduced pressure. Gas-chromatographic analysis showed a yield of 73% and an enantiomeric excess of >99%.

EXAMPLE 4

0.4 g of Celite 545 was suspended in 5 ml of 0.02 M histidine buffer (pH 6.8) and the mixture was shaken at room temperature for 2 hours. After removal of the swelling agent by filtration, 2.7 ml of an aqueous hydroxynitrile lyase solution (390 IU/ml) from *Pichia pastoris* were added dropwise and the mixture was stirred at room temperature for 15 min. A water content of 10% was then adjusted in a rotary evaporator. 176 mg of cinnamaldehyde (1.33 mmol) and 3 ml of diisopropyl ether (saturated with 0.02 M histidine buffer, pH 6.8) were then added at room temperature. After stirring at room temperature for 10 min, 200 μl of anhydrous hydrocyanic acid were added and the reaction vessel was sealed pressure-tight. The reaction mixture was allowed to react at room temperature for 1 hour, then the immobilized enzyme was filtered off, the precipitate was washed three times with 10 ml of diisopropyl ether each time and the organic phase was dried over anhydrous sodium sulfate. Removal of the solvent by distillation and subsequent purification by column chromatography afforded 171 mg of a slightly yellowish solid (81% isolated yield).

$[\alpha]_D^{20}$ −27.1° (c 1.85; $CHCl_3$).

2 mol equivalents of imidazole (147 mg) and 1.5 mol equivalents of TBDMS-Cl (243 mg) were dissolved in 10 ml of dry dimethylformamide with ice-cooling and the solution was stirred at room temperature for 15 min. The purified cyanohydrin was then added as a solid and the mixture was stirred at room temperature for 1 hour. It was then diluted with 15 ml of distilled water and the solution thus obtained was extracted twice with 15 ml of diethyl ether each time, dried using anhydrous sodium sulfate and the solvent was removed under reduced pressure. After column chromatography, 279 mg of pure (S)-(−)-2-((tert-butylmethylsilyl)oxy)-4-phenyl-(E)-but-3-enenitrile were obtained (95% isolated yield).

$[\alpha]_D^{20}$ −6.20° (c 0.55, $CHCl_3$). e.e.=92% (determined by gas chromatography)

$^1$H-NMR: δ (ppm) 0.21 (s, 3H); 0.24 (s, 3H); 0.97 (s, 9H); 5.14 (d, 1H); 6.20 (dd, 1H); 6.83 (d, 1H); 7.33–7.44 (m, 5H).

$^{13}$C-NMR: 135.17; 133.71; 128.83; 127.04; 123.77; 118.55; 62.73; 25.63; 18.26; −4.87; −4.92.

EXAMPLE 5

0.5 g of Avicel cellulose was suspended in 5 ml of 0.01 M sodium acetate buffer (pH 5.4) and shaken at room temperature for 1.5 hours. After filtration, the precipitate was treated with 2.7 ml of enzyme solution (390 IU/ml) from *Pichia pastoris* and stirred at room temperature for 0.5 hour. It was then concentrated to 30% water content in a rotary evaporator and suspended in 5 ml of diisopropyl ether. After addition of 230 μl of 3-phenoxybenzaldehyde (1.33 mmol), 200 μl of anhydrous hydrocyanic acid (5.25 mmol) were added, the reaction vessel was sealed pressure-tight and the mixture was allowed to react at room temperature for 2 hours. It was then diluted with 20 ml of diisopropyl ether, stirred at room temperature for 15 min, filtered off, the organic phase was dried using anhydrous sodium sulfate and the solvent was removed in vacuo. Purification by column chromatography afforded 293 mg of colorless oil (98% isolated yield).

$[\alpha]_D^{20}$ −27.9° (c 0.9, $CHCl_3$).

The purified cyanohydrin was dissolved in 20 ml of dry methylene chloride and reacted at room temperature overnight with 2 mol equivalents of acetic anhydride and 2 mol equivalents of pyridine. It was then washed with 20 ml each of 5% $H_2SO_4$, distilled water and saturated sodium hydrogencarbonate solution, dried using anhydrous sodium sulfate and the solvent was removed by distillation under reduced pressure. Purification by column chromatography afforded 338 mg of a colorless oil (97% isolated yield).

$[\alpha]_D^{20}$ −7.10° (c 1.0, $CHCl_3$). e.e.=94% (determined by gas chromatography)

$^1$H-NMR: δ (ppm) 2.18 (s, 3H); 6.36 (s, 1H); 7.01–7.44 (m, 9H).

$^{13}$C-NMR: 169.00; 158.52; 156.52; 133.80; 130.88; 130.24; 124.35; 122.33; 120.26; 119.64; 117.96; 116.12; 62.69; 20.66.

EXAMPLE 6

1.33 mmol of cyclohexanecarbaldehyde (161 μl) were dissolved in 2.7 ml of diisopropyl ether and the solution was cooled to 0–5° C. 1.1 ml of aqueous enzyme solution (900 IU/ml) and 200 μl of anhydrous hydrocyanic acid were added, the reaction vessel was sealed pressure-tight and the mixture was stirred at 0–5° C. for 1 hour. The mixture was then extracted three times with 5 ml of diisopropyl ether each time, dried using anhydrous sodium sulfate and the solvent was removed by distillation under reduced pressure. After column chromatography, 180 mg of a colorless oil (97% isolated yield) were obtained.

$[\alpha]_D^{20}$ −9.80° (c 1.25, $CHCl_3$).

Dissolution in 15 ml of methylene chloride, addition of 2 mol equivalents of acetic anhydride, 2 mol equivalents of pyridine, reaction overnight at room temperature and subsequent extraction with 20 ml each of 5% $H_2SO_4$, distilled water and saturated sodium hydrogencarbonate solution, drying with anhydrous sodium sulfate, removal of the solvent by distillation under reduced pressure and subsequent purification by column chromatography afforded 230 mg of a colorless, highly liquid oil (98% isolated yield).

$[\alpha]_D^{20}$ −64.8° (c 0.80, $CH_2Cl_2$). e.e.>99% (determined by gas chromatography)

$^1$H-NMR: δ (ppm) 1.11–1.30 (m, 5H); 1.69–1.91 (m, 6H); 2.13 (s, 3H); 5.16 (d, 1H).

$^{13}$C-NMR: 169.35; 116.35; 65.77; 40.21; 28.30; 28.08; 25.94; 25.54; 25.47; 20.49.

EXAMPLE 7

0.5 g of microcrystalline cellulose was allowed to swell at room temperature for 1 hour in 2.7 ml of 0.02 M histidine buffer. The swelling agent was then removed by filtration and the support was treated with 1.1 ml of aqueous enzyme solution (900 IU/ml). The precipitate was then adjusted to a water content of 25% in a rotary evaporator. The residue was suspended in 3 ml of diisopropyl ether (saturated with 0.02 M histidine buffer) and 1.33 mmol of furfural (220 µl) were added. After stirring at room temperature for 10 minutes, 5.25 mmol of anhydrous hydrocyanic acid (200 µl) were added, the flask was sealed pressure-tight and the reaction mixture was stirred at room temperature for 1 hour. The enzyme immobilizate was then filtered off and washed twice with 10 ml of diisopropyl ether each time. The combined organic phases were dried over anhydrous sodium sulfate and the solvent was removed under reduced pressure. Purification by column chromatography afforded the pure cyanohydrin as a colorless oil (160 mg, 98% isolated yield).

$[\alpha]_D^{20}$ −16.1° (c 1.2, $CHCl_3$).

The cyanohydrin purified in this way was dissolved in 15 ml of diethyl ether and treated with 2 mol equivalents of acetic anhydride and with 2 mol equivalents of pyridine. After a reaction time of 10 hours, the mixture was washed with 20 ml each of 5% $H_2SO_4$, distilled water and saturated sodium hydrogencarbonate solution, dried using anhydrous sodium sulfate and, after filtration, the solution was concentrated under reduced pressure. After column chromatography, 210 mg of a colorless oil were obtained (99% isolated yield).

$[\alpha]_D^{20}$ −23.3° (c 1.4, $CHCl_3$). e.e.=94% (determined by gas chromatography)

$^1$H-NMR: δ (ppm) 2.17 (s, 3H); 6.45 (dd, 1H); 6.47 (s, 1H); 6.68 (dd, 1H); 7.51 (dt, 1H).

$^{13}$C-NMR: 168.68; 145.10; 144.03; 112.64; 111.18; 114.17; 55.77; 20.38.

EXAMPLE 8

Analogously to Example 7, 157 mg of (−)-2-(3-furyl)-2-hydroxyacetonitrile (96% isolated yield) were obtained with furan-3-carbaldehyde after purification by column chromatography.

$[\alpha]_D^{20}$ −14.6° (c 1.85, $CHCl_3$).

After acetylation and appropriate work-up and purification by column chromatography, 208 mg of (−)-2-acetoxy-2-(3-furyl)acetonitrile were obtained (99% isolated yield).

$[\alpha]_D^{20}$ −11.4° (c 2, $CHCl_3$). e.e.=97% (determined by gas chromatography)

$^1$H-NMR: δ (ppm) 2.16 (s, 3H); 6.36 (s, 1H); 6.54 (dd, 1H); 7.47 (dd, 1H); 7.68 (m, 1H).

$^{13}$C-NMR: 169.15; 144.77; 142.75; 118.34; 109.46; 115.86; 55.78; 20.63.

EXAMPLE 9

1.33 mmol of hexanal (133 mg) were dissolved in 3 ml of water-saturated diisopropyl ether. 1.1 ml of aqueous hydroxynitrile lyase solution (900 IU/ml) were added at room temperature and the mixture was stirred at room temperature for 5 min. 300 µl of anhydrous hydrocyanic acid (7.88 mmol) were then added and the reaction vessel was sealed pressure-tight. After stirring at room temperature for 1.5 hours, the phases were separated, the aqueous phase was extracted three times with 5 ml of diisopropyl ether each time and the combined ether phases were dried using anhydrous sodium sulfate. The solvent was removed under reduced pressure and the crude cyanohydrin obtained in this way was subjected to purification by column chromatography. 140 mg of (S)-2-hydroxyheptanenitrile were obtained (83% isolated yield).

$[\alpha]_D^{20}$ −14.1° (c 1.5, $CHCl_3$).

The purified cyanohydrin was dissolved in 5 ml of dry diethyl ether, and the solution was treated with 2 mol equivalents of acetic anhydride and 2 mol equivalents of pyridine and stirred at room temperature for 8 hours. It was then extracted with 10 ml each of 5% $H_2SO_4$, distilled water and saturated $NaHCO_3$ solution, dried over anhydrous sodium sulfate and the solvent was removed under reduced pressure. After purification by column chromatography, 182 mg of (S)-2-acetoxyheptanenitrile were obtained (98% isolated yield). e.e.=96% (determined by gas chromatography)

$^1$H-NMR: δ (ppm) 0.90 (t, 3H); 1.21–1.60 (m, 6H); 1.90 (q, 2H); 2.15 (s, 3H); 5.32 (t, 1H).

$^{13}$C-NMR: 169.1; 116.9; 61.10; 32.11; 30.89; 24.10; 22.23; 20.29; 13.76.

EXAMPLE 10

2 mmol of 2-pentanone (21 µl) were dissolved in 10 ml of diisopropyl ether and cooled to 0–5° C. with stirring. 4 mmol of potassium cyanide (260 mg) were then treated with 0.1 M citric acid at 0–5° C. so that a pH of 3.5 was achieved. This aqueous solution was added to the organic phase. After addition of 1000 IU of Hnl (1 ml of enzyme solution (1000 IU/ml)), the reaction vessel was sealed pressure-tight and the mixture was stirred at 0–5° C. for 1.5 hours. The mixture was then diluted with 10 ml of diisopropyl ether and the reaction mixture was extracted therewith, and the aqueous phase was separated off and extracted a second time with 20 ml of diisopropyl ether. The combined organic phases were dried over anhydrous sodium sulfate and concentrated to dryness under reduced pressure. 136 mg (60%) of a slightly yellowish oil were obtained. After column chromatography, the pure cyanohydrin was obtained in 38% yield (86 mg) as a colorless oil.

$[\alpha]_D^{20}$ −2.5° (c 1.46, $CHCl_3$).

The purified cyanohydrin was dissolved in 2 ml of absolute methylene chloride and the solution was treated at room temperature with 2 mol equivalents of acetic anhydride and with 2 mol equivalents of pyridine and stirred at room temperature for 34 hours with exclusion of moisture. 350 µl of absolute methanol were then added and the mixture was stirred at room temperature for 0.5 hour. It was then diluted with 10 ml of methylene chloride and extracted with 10 ml each of 5% $H_2SO_4$, distilled water and saturated $NaHCO_3$ solution and dried over anhydrous sodium sulfate and the solvent was removed under reduced pressure. 112 mg (95%)

of (S)-2-acetoxy-2-methylpentanenitrile were obtained. e.e.=75% (determined by gas chromatography)

[α]$_D^{20}$ −8.5° (c 1.94, CHCl$_3$)

$^1$H-NMR: δ (ppm) 0.99 (t, 3H); 1.41–1.70 (m, 2H); 1.73 (s, 3H); 1.77–2.04 (m, 2H); 2.09 (s, 3H);

$^{13}$C-NMR: 168.88; 118.83; 72.00; 41.79; 24.60; 21.17; 17.33; 13.75.

EXAMPLE 11

500 µl of 3-methyl-2-pentanone (4 mmol) were dissolved in 15 ml of diisopropyl ether with stirring, the mixture was cooled to 0–5° C. and an aqueous solution of 520 mg. of potassium cyanide in 20 ml of 0.5 M citric acid was added. After addition of 2 ml of enzyme solution (1000 IU/ml), the reaction vessel was sealed pressure-tight and the mixture was stirred at 0–5° C. for 5 hours. The mixture was then diluted with 30 ml of diisopropyl ether and the reaction mixture was extracted. After separation of the organic phase, the aqueous phase was extracted a second time by shaking with 30 ml of diisopropyl ether. The aqueous phase was discarded, the combined organic phases were dried over anhydrous sodium sulfate and the solvent was removed by distillation under reduced pressure. After column chromatography, 193 mg of (S)-2-hydroxy-2,4-dimethylpentanenitrile (38%) were obtained.

Derivatization and subsequent work-up by the manner described in Example 10 afforded 231 mg of (S)-2-acetoxy-2,4-dimethylpentanenitrile (90%) as a colorless oil.

[α]$_D^{20}$ −28.5° (c 1.75, CHCl$_3$) e.e.=96% (determined by gas chromatography)

$^1$H-NMR: δ (ppm) 1.01; 1.04 (2d, 6H); 1.43 (s, 2H); 1.75 (s, 3H); 1.83–2.04 (m, 1H); 2.09 (s, 3H)

$^{13}$C-NMR: 168.87; 119.04; 71.69; 30.36; 25.22; 24.84; 23.68; 23.52; 21.29.

EXAMPLE 12

10 mmol of pinacolone (1.25 g) were dissolved in 30 ml of methyl t-butyl ether, treated with 5 ml of enzyme solution (1000 IU/ml) and cooled to 0–5° C. with stirring. Parallel to this, 20 mmol of potassium cyanide were dissolved in 250 ml of 0.1 M aqueous citric acid with ice-cooling. The hydrocyanic acid solution prepared in this way was added to the reaction mixture and the reaction vessel was sealed pressure-tight. After a reaction time of 2.5 h, the mixture was diluted with 50 ml of methyl t-butyl ether and the reaction solution was extracted. The aqueous phase was separated off, extracted by shaking again with 80 ml of methyl t-butyl ether and then discarded. The combined organic phases were dried using anhydrous sodium sulfate and the solvent was removed under reduced pressure. After column chromatography, 0.95 g of (S)-2-hydroxy-2,3,3-trimethylbutanenitrile (75%) was obtained as a white solid (m.p. 98–99° C.).

The crude product was then dissolved in 10 ml of anhydrous diethyl ether and 2.5 mol equivalents each of acetyl chloride and pyridine were added with ice-cooling. After addition of 30 mg of 4-N,N-dimethylaminopyridine, the mixture was allowed to react at room temperature for 48 hours. 3 mol equivalents of dry methanol were then added and the mixture was stirred at room temperature for a further 30 min. Finally, this solution was diluted with 20 ml of diethyl ether and extracted with 30 ml each of dilute, aqueous sulfuric acid, distilled water and saturated, aqueous sodium hydrogencarbonate solution. After drying using anhydrous sodium sulfate, the solvent was removed under reduced pressure. After column chromatography, 1.21 g of (S)-2-acetoxy-2,3,3-trimethylbutanenitrile (96%) were obtained as a colorless oil.

[α]$_D^{20}$ −40.5° (c 2.25, CHCl$_3$) e.e.=78% (determined by gas chromatography)

$^1$H-NMR: 1.11 (s, 9H); 1.69 (s, 3H); 2.09 (s, 3H).

$^{13}$C-NMR: 168.97; 118.10; 78.07; 38.39; 24.66; 21.20; 18.93.

EXAMPLE 13

Single Use of Immobilized (S)-Hnl from *Pichia pastoris* in ethyl acetate 2 g of Avicel were swollen for 1 hour in 13.4 ml of 0.02 M sodium acetate solution (pH 5.4). The mixture was then filtered and the residue was treated for 5 minutes with 13.4 ml of enzyme solution (390 IU/ml). Water was carefully removed by distillation at 40° C. and 10–20 mbar. The water content of immobilizate after this treatment was 40%.

13.5 ml of ethyl acetate which was saturated beforehand with 0.01 M sodium acetate solution were introduced. The immobilizate was stirred into this. 0.71 g of freshly distilled benzaldehyde (6.6 mmol) and 1.00 ml of hydrocyanic acid (25.5 mmol) were added at 20° C. The course of the reaction was monitored photometrically by the decrease in the concentration of benzaldehyde. After 1 hour, a reaction conversion of 95% was achieved. The reaction solution was filtered and washed a number of times with 10 ml of ethyl acetate. The filtrate was concentrated in vacuo. 0.8 g of S-mandelonitrile (90% chemical yield) having an enantiomeric excess of 98% remained as a residue.

EXAMPLE 14

Repeated Use of Immobilized (S)-Hnl from *Pichia pastoris* in ethyl acetate 1 g of Avicel was swollen for 1 hour in 6.7 ml of 0.02 M sodium acetate solution (pH 5.4). The mixture was then filtered and the residue was treated with 1.68 ml of enzyme solution (330 IU/ml) for 5 minutes. Water was carefully removed by distillation at 40° C. and 10–20 mbar. After this treatment, the water content of the immobilizate was 40%.

13.5 ml of ethyl acetate which was saturated beforehand with 0.01 M sodium acetate solution were introduced. The immobilizate was stirred into this. 0.71 g of freshly distilled benzaldehyde (8.8 mmol) and 1.0 ml of hydrocyanic acid (25.5 mmol) were added at 20° C. The course of the reaction was monitored by the decrease in the concentration of benzaldehyde. After 45 minutes, a reaction conversion of 90% was achieved. The reaction solution was filtered and washed a number of times with 10 ml of ethyl acetate. The filtrate was concentrated in vacuo. 0.86 g of S-mandelonitrile having an enantiomeric excess of 98.4 remained as a residue.

The immobilizate which was filtered off was stirred into further batches having the same initial weights as already described above and the mixture was worked up in the same manner.

Results:

|         | g of (S)-mandelonitrile | % of theory | % ee |
|---------|------------------------|-------------|------|
| 1st use | 0.86                   | 97          | 98.4 |
| 2nd use | 0.74                   | 83          | 97.2 |
| 3rd use | 0.76                   | 85          | 94.1 |

EXAMPLE 15

Repeated Use of Immobilized (S)-Hnl from *Pichia pastoris* in methyl tert-butyl ether (MTBE)

2 g of Avicel were swollen for 1 hour in 13.4 ml of 0.02 M sodium acetate solution (pH 5.4). The mixture was then filtered and the residue was treated for 5 minutes with 3.35 ml of enzyme solution (330 IU/ml). Water was carefully removed by distillation at 40° C. and 10–20 mbar. The water content of the immobilizate was 40% after this treatment.

13.5 ml of MTBE which was saturated beforehand with 0.01 M sodium acetate solution were introduced. The immobilizate was stirred into this. 0.71 g of freshly distilled benzaldehyde (6.6 mmol) and 1.00 ml of hydrocyanic acid (25.5 mmol) were added at 20° C. The course of the reaction was monitored photometrically by the decrease in the concentration of benzaldehyde. After 45 minutes, the conversion was 90%.

The immobilizate which was filtered off was stirred into further batches having the same initial weights as already described above and worked up in the same manner.
Results:

|         | g of (S)-mandelonitrile | % of theory | % ee |
|---------|------------------------|-------------|------|
| 1st use | 0.75                   | 84          | 98.9 |
| 2nd use | 0.77                   | 86          | 98.0 |
| 3rd use | 0.73                   | 82          | 96.8 |
| 4th use | 0.71                   | 80          | 88.3 |

EXAMPLE 16

Repeated Use of Immobilized (S)-Hnl from *Pichia pastoris* in diisopropyl ether (DIPE)

2 g of Avicel were swollen for 1 hour in 13.4 ml of 0.02 M sodium acetate solution (pH 5.4). The mixture was then filtered and the residue was treated for 5 minutes with 3.35 ml of enzyme solution (330 IU/ml). Water was carefully removed by distillation at 40° C. and 10–20 mbar. The water content of the immobilizate after this treatment was 40%. 13.5 ml of MTBE which was saturated beforehand with 0.01 M sodium acetate solution were introduced. The immobilizate was stirred into this. 0.71 g of freshly distilled benzaldehyde (6.6 mmol) and 1.00 ml of hydrocyanic acid (25.5 mmol) were added at 20° C. The course of the reaction was monitored photometrically by the decrease in the concentration of benzaldehyde. After 1 hour, the conversion was more than 90%.

The immobilizate which was filtered off was stirred into further batches having the same initial weights as already described above and worked up in the same manner.

Results:

|         | g of (S)-mandelonitrile | % of theory | % ee |
|---------|------------------------|-------------|------|
| 1st use | 0.74                   | 83          | 97.9 |
| 2nd use | 0.72                   | 81          | 97.7 |
| 3rd use | 0.72                   | 82          | 95.0 |
| 4th use | 0.75                   | 84          | 96.8 |
| 5th use | 0.77                   | 86          | 95.4 |
| 6th use | 0.77                   | 86          | 94.7 |
| 7th use | 0.75                   | 84          | 92.5 |

EXAMPLE 17

Single Use of a Minimal Amount of Immobilized (S)-Hnl from *Pichia pastoris* in diisopropyl ether (DIPE)

1 g of Avicel was swollen for 1 hour in 6.7 ml of 0.07 M sodium acetate solution (pH 5.4). The mixture was then filtered and the residue was treated for 5 minutes with 0.8 ml of enzyme solution (194 IU/ml). Water was carefully removed by distillation at 40° C. and 10–20 mbar. The water content of the immobilizate after this treatment was 40%.

13.5 ml of DIPE which was saturated beforehand with 0.01 M sodium acetate solution were introduced. The immobilizate was stirred into this. 0.71 g of freshly distilled benzaldehyde (6.6 mmol) and 1.0 ml of hydrocyanic acid (25.5 mmol) were added at 20° C. The course of the reaction was monitored photometrically by the decrease in the concentration of benzaldehyde. After 2 hours, the conversion was 86%.
Results:

|         | g of (S)-mandelonitrile | % of theory | % ee |
|---------|------------------------|-------------|------|
| 1st use | 0.86                   | 97          | 96.5 |

EXAMPLE 18

Single Use of Immobilized (S)-Hnl from *Pichia pastoris* in ethyl acetate and acetone cyanohydrin as a cyanide Donor 2 g of Avicel were swollen for 1.6 hours in 13.5 ml of 0.02 M sodium acetate solution (pH 5.4). The mixture was then filtered and the residue was treated for 5 minutes with 3.35 ml of enzyme solution (390 IU/ml). Water was carefully removed by distillation at 40° C. and 10–20 mbar. The water content of the immobilizate after this treatment was 40%.

13.5ml of ethylacetate which was saturated beforehand with 0.01 M sodium acetate solution were introduced. The immobilizate was stirred into this. 0.71 g of freshly distilled benzaldehyde (6.6 mmol) and 3.3 ml of freshly distilled acetone cyanohydrin (33.8 mmol) were added at 20° C. The course of the reaction was monitored photometrically by the decrease in the concentration of benzaldehyde. The conversion was 78% after 4 hours.

The reaction solution was filtered and washed a number of times with 10 ml of ethyl acetate. The filtrate was concentrated in vacuo. In addition to unreacted acetone cyanohydrin, the residue contained the desired (S)-mandelonitrile having an enantiomeric excess of 95.0%.

EXAMPLE 19

Repeated Use of Nonimmobilized (S)-Hnl from *Pichia pastoris* in diisopropyl ether (DIPE) in a Two-phase Mixture 13.5 ml of DIPE which was saturated beforehand with 0.01 M sodium acetate solution were introduced. 1.6 ml of enzyme solution (194 IU/ml) were stirred into this. 0.71 g of freshly distilled benzaldehyde (6.6 mmol) and 1.0 ml of hydrocyanic acid (25.5 mmol) were added at 20° C. The course of the reaction was monitored photometrically by the decrease in the concentration of benzaldehyde.

The phases of the reaction solution were separated. The aqueous phase was treated a number of times with DIPE. The DIPE solutions thus obtained were combined and added to the reaction solution. The solvent was removed by distillation at 40° C. and 20 mbar. (S)-Mandelonitrile remained as a residue.

The aqueous enzyme solution was employed in the next batches using the same initial weights.
Results:

|  | Hours/ conversion | g of (S)-mandelonitrile | % of theory | % ee |
|---|---|---|---|---|
| 1st use | 1.0/93 | 0.80 | 90 | 99.1 |
| 2nd use | 1.5/86 | 0.81 | 91 | 98.7 |
| 3rd use | 2.0/90 | 0.71 | 80 | 99.0 |
| 4th use | 3.5/79 | 0.79 | 89 | 97.5 |

EXAMPLE 20

Single Use of a Minimal Amount of Nonimmobilized (S)-Hnl from *Pichia pastoris* in diisopropyl ether (DIPE) in a Two-phase Mixture 13.5 ml of DIPE which was saturated beforehand with 0.01 M sodium acetate solution were introduced. 0.8 ml of enzyme solution (194 IU/ml) were stirred into this. 0.71 g of freshly distilled benzaldehyde (6.6 mmol) and 1.0 ml of hydrocyanic acid (25.5 mmol) were added at 20° C. The course of the reaction was monitored photometrically by the decrease in the concentration of benzaldehyde.

The phases of the reaction solution were separated. The aqueous phase was treated a number of times with DIPE. The DIPE solutions thus obtained were combined and added to the reaction solution. The solvent was removed by distillation at 40° C. and 20 mbar. (S)-Mandelonitrile remained as a residue.
Results:

|  | Hours/ conversion | g of (S)-mandelonitrile | % of theory | % ee |
|---|---|---|---|---|
| 1st use | 2.0/86 | 0.86 | 97 | 99.1 |

EXAMPLE 21

Repeated Use of Nonimmobilized (S)-Hnl from *Pichia pastoris* in methyl tert-butyl ether in a Two-phase Mixture 13.5 ml of MTBE which was saturated beforehand with 0.01 M sodium acetate solution were introduced. 5.5 ml of enzyme solution (194 IU/ml) were stirred into this. 0.71 g of freshly distilled benzaldehyde (6.6 mmol) and 1.0 ml of hydrocyanic acid (25.5 mmol) were added at 20° C. The course of the reaction was monitored photometrically by the decrease in the concentration of benzaldehyde.

The phases of the reaction solution were separated. No isolation of (S)-mandelonitrile took place, only the activity of the enzyme solution was measured. The aqueous enzyme solution was employed in the next batches using the same initial weights.
Results:

|  | Hours/conversion | Activity (IU/ml) |
|---|---|---|
| 1st use | 1/92.5% | 194 |
| 2nd use | 0.75/93.6% | 119 |
| 3rd use | 0.75/87.2 | 81.5 |
| 4th use | 1.5/87.4 | 61.4 |

EXAMPLE 22

Single Use of a Minimal Amount of Nonimmobilized (S)-Hnl from *Pichia pastoris* in methyl tert-butyl ether (MTBE) in a Two-phase Mixture 13.5 ml of MTBE which was saturated beforehand with 0.01 M sodium acetate solution were introduced. 0.8 ml of enzyme solution (194 IU/ml) was stirred into this. 0.71 g of freshly distilled benzaldehyde (6.6 mmol) and 1.0 ml of hydrocyanic acid (25.5 mmol) were added at 20° C. The course of the reaction was monitored photometrically by the decrease in the concentration of benzaldehyde.

The phases of the reaction solution were separated. The aqueous phase was treated a number of times with MTBE. The MTBE solutions thus obtained were combined and added to the reaction solution. The solvent was removed by distillation at 40° C. and 20 mbar. (S)-Mandelonitrile remained as a residue.
Results:

|  | Hours/ conversion | g of (S)-mandelonitrile | % of theory | % ee |
|---|---|---|---|---|
| 1st use | 2.0/86 | 0.85 | 96 | 99.0 |

EXAMPLE 23

Single Use of a Minimal Amount of Nonimmobilized (S)-Hnl from *Pichia pastoris* in methyl tert-butyl ether (MTBE) in a two-phase mixture Using Differing Volumes of Water 13.5 ml of MTBE which was saturated beforehand with 0.01 M sodium acetate solution were introduced. 0.8 ml of enzyme solution (194 IU/ml) with differing amounts of water was stirred into this. 0.71 g of freshly distilled benzaldehyde (6.6 mmol) and 1.0 ml of hydrocyanic acid (25.5 mmol) were added at 20° C. The course of the reaction was monitored photometrically by the decrease in the concentration of benzaldehyde.

The phases of the reaction solution were separated. The aqueous phase was treated a number of times with MTBE. The MTBE solutions thus obtained were combined and added to the reaction solution. The solvent was removed by distillation at 40° C. and 20 mbar. (S)-Mandelonitrile remained as a residue.
Results:

| Addition of water | Hours/ conversion | g of (S)-mandelonitrile | % of theory | % ee |
|---|---|---|---|---|
| 1.2 ml | 2.0/86 | 0.88 | 99 | 98.3 |
| 3.2 ml | 1.0/90 | 0.80 | 90 | 98.4 |
| 9.2 ml | 1.0/89 | 0.86 | 97 | 97.5 |

EXAMPLE 24

Single Use of a Minimal Amount of Nonimmobilized (S)-Hnl from *Pichia pastoris* in methyl tert-butyl ether (MTBE) in a Two-phase Mixture at Differing pHs 13.5 ml of MTBE which was saturated beforehand with 0.01 M sodium acetate solution were introduced. 0.8 ml of enzyme solution (194 IU/ml) and 9.2 ml of water were stirred into this. Before the addition, the pH was adjusted with phosphoric acid. 0.71 g of freshly distilled benzaldehyde (6.6 mmol) and 1.0 ml of hydrocyanic acid (25.5 mmol) were added at 20° C. The course of the reaction was monitored photometrically by the decrease in the concentration of benzaldehyde.

The phases of the reaction solution were separated. The aqueous phase was treated a number of times with MTBE. The MTBE solutions thus obtained were combined and added to the reaction solution. The solvent was removed by distillation at 40° C. and 20 mbar. (S)-Mandelonitrile remained as a residue.
Results:

| pH | Hours/ conversion | g of (S)-mandelonitrile | % of theory | % ee |
|---|---|---|---|---|
| 5.7 | 1.0/89 | 0.88 | 97 | 97.5 |
| 5.0 | 1.0/90 | 0.85 | 0.5 | 98.8 |
| 4.0 | 22.0/67 | no isolation | | |
| 3.0 | 22.0/11 | no isolation | | |

EXAMPLE 25

Single Use of a Minimal Amount of Nonimmobilized (S)-Hnl from *Pichia pastoris* in methyl tert-butyl ether (MTBE) in a Two-phase Mixture with a Decreased Amount of Solvent 6.7 ml of MTBE which was saturated beforehand with 0.01 M sodium acetate solution were introduced. 0.8 ml of enzyme solution (194 IU/ml) was stirred into this. 0.71 g of freshly distilled benzaldehyde (6.6 mmol) and 1.0 ml of hydrocyanic acid (25.5 mmol) were added at 20° C. The course of the reaction was monitored photometrically by the decrease in the concentration of benzaldehyde.

The phases of the reaction solution were separated. The aqueous phase was treated a number of times with MTBE. The MTBE solutions thus obtained were combined and added to the reaction solution. The solvent was removed by distillation at 40° C. and 20 mbar. (S)-Mandelonitrile remained as a residue.
Results:

| | Hours/ conversion | g of (S)-mandelonitrile | % of theory | % ee |
|---|---|---|---|---|
| 1st use | 2.0/92 | 0.88 | 99 | 94.4 |

EXAMPLE 26

Repeated Use of Nonimmobilized (S)-Hnl from *Pichia pastoris* in methyl tert-butyl ether (MTBE) in a Two-phase Mixture with Addition of a Stabilizer 13.5 ml of MTBE which was saturated beforehand with 0.01 M sodium acetate solution were introduced. 5.5 ml of enzyme solution (151 IU/ml) and 55 mg of a nonactive Hnl preparation from leaves of *Hevea brasiliensis* were stirred into this. 0.71 g of freshly distilled benzaldehyde (6.6 mmol) and 1.0 ml of hydrocyanic acid (25.5 mmol) were added at 20° C. The course of the reaction was monitored photometrically by the decrease in the concentration of benzaldehyde.

The phases of the reaction solution were separated. The aqueous phase was treated a number of times with MTBE. The MTBE solutions thus obtained were combined and added to the reaction solution. The solvent was removed by distillation at 40° C. and 20 mbar. (S)-Mandelonitrile remained as a residue.

The aqueous enzyme solution was employed in the next batches using the same initial weights. 0.5 ml of water was added in the 10th and 11th use.
Results:

| Use | Hours/ conversion | g of (S)-mandelonitrile | % of theory | % ee |
|---|---|---|---|---|
| 1st | 1/91 | 0.78 | 88 | 97.6 |
| 2nd | 1/89 | 0.60 | 67 | 97.8 |
| 3rd | 1/92 | 0.87 | 98 | 97.2 |
| 4th | 1/93 | 0.87 | 98 | 98.2 |
| 5th | 1/97 | 0.86 | 97 | 97.1 |
| 6th | 1/96 | 0.88 | 99 | 98.6 |
| 7th | 1/90 | 0.88 | 99 | 99.1 |
| 8th | 1/94 | 0.88 | 99 | 98.4 |
| 9th | 2/86 | 0.89 | 100 | 97.8 |
| 10th | 1/93 | 0.85 | 96 | 98.4 |
| 11th | 2/93 | 0.83 | 93 | 98.9 |

EXAMPLE 27

Repeated Use of Nonimmobilized (S)-Hnl in Disrupted Cells of *Pichia pastoris* ("Homogenate") in diisopropyl ether (DIPE) in a Two-phase Mixture 13.5 ml of DIPE which was saturated beforehand with 0.01 M sodium acetate solution were introduced. 3.2 ml of homogenate (310 IU/ml) were stirred into this. 0.71 g of freshly distilled benzaldehyde (6.6 mmol) and 1.0 ml of hydrocyanic acid (25.5 mmol) were added at 20° C. The course of the reaction was monitored photometrically by the decrease in the concentration of benzaldehyde.

The phases of the reaction solution were separated. The aqueous phase was treated a number of times with DIPE.

The DIPE solutions thus obtained were combined and added to the reaction solution. The solvent was removed by distillation at 40° C. and 20 mbar. (S)-Mandelonitrile remained as a residue.

The aqueous enzyme solution was employed in the next batches using the same initial weights. 3 ml of water were added in the 5th use.

Results:

| Use | Hours/ conversion | g of (S)-mandelonitrile | % of theory | % ee |
| --- | --- | --- | --- | --- |
| 1st | 1/88 | 0.82 | 92 | 95.5 |
| 2nd | 1/87 | 0.76 | 85 | 95.3 |
| 3rd | 1.5/91 | 0.87 | 98 | 95.2 |
| 4th | 1.5/94 | 0.88 | 99 | 92.9 |
| 5th | 1/92 | 0.88 | 99 | 98.2 |
| 6th | 1/91 | 0.88 | 99 | 97.9 |
| 7th | 2/85 | 0.87 | 98 | 96.3 |

What is claimed is:

1. An enantioselective process for the preparation of the (S)-enantiomer of an optically active cyanohydrin by reaction of an aldehyde or of a ketone with a cyanide group donor, which comprises reacting the aldehyde or the ketone with a cyanide group donor in an organic diluent in the presence of a recombinant (S)-hydroxynitrile lyase from *Hevea brasiliensis* and isolating the (S)-cyanohydrin formed from the reaction mixture.

2. The process as claimed in claim 1, wherein an aliphatic, aromatic or heteroaromatic aldehyde or an unsymmetrical ketone is reacted.

3. The process as claimed in claim 1, wherein the cyanide group donor employed is hydrocyanic acid or a cyanohydrin of the formula $(R_1)(R_2)C(OH)(CN)$, in which $R_1$ and $R_2$ are alkyl groups.

4. The process as claimed in claim 3, wherein the cyanide group donor is hydrocyanic acid or acetone cyanohydrin.

5. The process as claimed in claim 1, wherein recombinant (S)-hydroxynitrile lyase prepared from *Pichia pastoris* or *Saccharomyces cerevisiae* is employed.

6. The process as claimed in claim 1, wherein the (S)-hydroxynitrile lyase is immobilized or employed in a two-phase system.

7. The process as claimed in claim 1, wherein the (S)-hydroxynitrile lyase can be reused a number of times.

8. The process as claimed in claim 1, wherein the organic diluent used is a water-immiscible aliphatic or aromatic hydrocarbon, alcohol, ether or ester.

9. The process as claimed in claim 1, wherein the organic diluent used is ethyl acetate, diisopropyl ether, methyl tert-butyl ether or dibutyl ether.

* * * * *